(12) United States Patent
Torbati

(10) Patent No.: US 7,914,469 B2
(45) Date of Patent: Mar. 29, 2011

(54) CELLULITE ULTRASOUND TREATMENT

(75) Inventor: Eldad Torbati, Bat Yam (IL)

(73) Assignee: Real Aesthetics Ltd., Jerusalem (IL)

(*) Notice: Subject to any disclaimer, the term of this patent is extended or adjusted under 35 U.S.C. 154(b) by 791 days.

(21) Appl. No.: 10/549,398

(22) PCT Filed: Mar. 11, 2004

(86) PCT No.: PCT/IL2004/000238
§ 371 (c)(1),
(2), (4) Date: Jun. 19, 2006

(87) PCT Pub. No.: WO2004/080147
PCT Pub. Date: Sep. 23, 2004

(65) Prior Publication Data
US 2007/0055154 A1  Mar. 8, 2007

(51) Int. Cl.
*A61H 1/00* (2006.01)
*A61B 8/00* (2006.01)

(52) U.S. Cl. ............................. 601/2; 600/439

(58) Field of Classification Search .......... 601/2
See application file for complete search history.

(56) References Cited

U.S. PATENT DOCUMENTS

| | | | |
|---|---|---|---|
| 2,830,578 A | | 4/1958 | DeGroff |
| 3,735,756 A | | 5/1973 | Richards et al. |
| 4,767,402 A | * | 8/1988 | Kost et al. ............ 604/22 |
| 5,413,550 A | * | 5/1995 | Castel .................. 601/2 |
| 5,573,552 A | * | 11/1996 | Hansjurgens ......... 607/68 |
| 6,190,315 B1 | * | 2/2001 | Kost et al. ............ 600/309 |
| 6,350,276 B1 | | 2/2002 | Knowlton |
| 6,405,072 B1 | * | 6/2002 | Cosman ............... 600/426 |
| 6,405,572 B1 | * | 6/2002 | Seamans ............. 70/456 R |
| 6,443,914 B1 | | 9/2002 | Costantino |
| 6,517,499 B1 | * | 2/2003 | Pereira ................ 601/7 |
| 2002/0193831 A1 | * | 12/2002 | Smith, III ............ 607/2 |
| 2003/0032900 A1 | | 2/2003 | Ella |
| 2003/0069618 A1 | * | 4/2003 | Smith et al. .......... 607/100 |
| 2004/0019286 A1 | * | 1/2004 | Lia et al. ............. 600/491 |
| 2004/0138712 A1 | * | 7/2004 | Tamarkin et al. ..... 607/3 |
| 2004/0260209 A1 | * | 12/2004 | Ella et al. ............ 601/7 |

FOREIGN PATENT DOCUMENTS

| | | |
|---|---|---|
| DE | 948351 | 8/1956 |
| DE | 19613425 | 1/1997 |
| EP | 1219278 | * 11/2001 |

(Continued)

OTHER PUBLICATIONS

International Preliminary Report on Patentability (Form PCT/IPEA/409) Oct. 21, 2005.

(Continued)

*Primary Examiner* — Eric F Winakur
*Assistant Examiner* — Hien Nguyen
(74) *Attorney, Agent, or Firm* — Edwards Angell Palmer & Dodge LLP

(57) ABSTRACT

A treatment system and method for reducing body perimeter, primarily aimed at reducing cellulite and/or fat at a region of treatment. Ultrasound waves and pressure exertion are applied to the region of treatment, preferably simultaneously. The pressure exersion may include manual or mechanical massage, and/or electrical muscle stimulation. An optional ultrasonic transducer head is utilized to apply also pressure and massage. Preferable frequencies and intensities of the ultrasound and the stimulation are also provided.

61 Claims, 7 Drawing Sheets

FOREIGN PATENT DOCUMENTS

| | | |
|---|---|---|
| EP | 1219278 | 7/2002 |
| EP | 1219278 A2 * | 7/2002 |
| GB | 2261603 | 5/1993 |
| GB | 2 303 552 | 2/1997 |
| JP | 09-248213 | 9/1997 |
| JP | 11-332943 | 12/1999 |
| JP | 2000-060928 | 2/2000 |
| JP | 2001-170128 | 6/2001 |
| JP | 2001-286484 | 10/2001 |
| WO | WO-02/054018 | 7/2002 |
| WO | WO-02/092168 | 11/2002 |

OTHER PUBLICATIONS

International Search Report (Form PCT/ISA/210) from corresponding international application No. PCT/US2004/00238, 3 pages.

"Written Opinion" (Form PCT/ISA/237) from corresponding international application No. PCT/IL2004/00238, 5 pages.

Elettronica Pagani SRL, Operating Manual, Nov. 5, 2001.

Decision on Grant in corresponding Russian Application No. 2005131621 together with Abstract and Allowed claims.

Information on Acceptance by the Australian Patent Office of corresponding Australian Patent Application No. 2004218906.

Allowed claims for corresponding Australian Patent Application No. 2004218906.

Dr. Roman Karaev, *Beauty Therapy Manual*, Moscow, Russia 1999 (translation of title page only).

BTL-5000 Electrotherapy User's Guide, v110z2RK Jan. 15, 2003.

Iskra Medical Medio Sono, Iskra Medical, 2001 (informational pamphlet).

Sonopuls 490, Compact Unit for Ultrasoundtherapy, Ernaf Nonius (informational pamphlet).

* cited by examiner

CELLULITE ULTRASOUND TREATMENT

CROSS-REFERENCE TO RELATED APPLICATIONS

This is a national stage filing which is based on and claims priority to and the benefit of International Application Number PCT/IL2004/000238 which itself is based on and claims priority to and the benefit of U.S. Provisional Patent Application Number 60/454,799. International Application Number PCT/IL2004/000238 was filed on Mar. 11, 2004, and it was published as International Publication Number WO 2004/080147 on Sep. 23, 2004. U.S Provisional Patent Application Number 60/454,799 was filed on Mar. 13, 2003. The entirety of both of these applications is incorporated herein by reference.

FIELD OF THE DISCLOSED TECHNIQUE

The disclosed technique relates to a method and apparatus for reducing body perimeter, fat, and cellulite in general, and to techniques employing ultrasound in particular.

BACKGROUND OF THE DISCLOSED TECHNIQUE

Cellulite is a condition present in around 90% of post-adolescent women irrespective of obesity or thinness, and rarely appearing to the same extent in men. Cellulite is characterized by unsmooth skin spotted with dimples and ridges, leaving the skin with a texture resembling an orange peel. Occasionally, stretch marks may result as well. Cellulite occurs mainly in the regions of the thighs, knees, buttocks, abdomen, and arms. The condition can be attributed to the buildup pattern of fat cells in superficial pockets of trapped fat, leading to modifications in the surrounding connective tissues and to an altered blood and lymph circulation.

Contemporary research provides support to theories for the formation of cellulite fat, as briefly described below. The skin structure and underlying layers in the human body can be seen in the illustration of FIG. 1 (disclosed in the following website: http://www.cellulite.com/what is cellulite.htm,© 2002 Cellulite Formula™). Under the dermis and epidermis layers of the skin are two layers of fat, an upper fat layer and a lower fat layer. Cellulite develops in the upper fat layer, known as the upper hypodermis or subcutaneous fat layer. The fat in this area is organized into chambers, or fat lobes, held in place by collagen fibers of fascia, a connective tissue that anchors the skin to the muscle. As the fat in these chambers increases, the fascia does not stretch; fat therefore accumulates in the chambers and the dimpling cellulite effect results. The weakened fascia allows the fat mass, normally contained in well organized chambers, to project upward into the dermis layer.

The connective tissue in the subcutaneous layer of the skin is surrounded by fat cells. A proper supply of nutrients and oxygen in the blood supply keeps the fatty tissue well nourished, and a good drainage system by the veins and the lymph channels constantly removes waste products. Normal fatty tissue is smooth, well nourished, and free from toxins and excess fluid; but if the blood supply or drainage system becomes disrupted or constricted, then a gradual build-up of toxins and fluid within the fatty tissue may occur. As a result, the body does not succeed in breaking down the accumulated fat and to remove it from the system. This fat is not properly absorbed into the blood, and swells up with excess fluids to produce pockets of cellulite, thus stretching the connective tissues and leaving a lumpy appearance on the skin. As the cellulite condition worsens, the vertical connective tissue thickens and hardens, creating ridges and accentuating the dimpled skin appearance. As one ages, the layer of skin thins, resulting in the rippling cellulite effect.

On the whole, the cellulite formation process is believed to involve several propagating mechanisms. The lumping of fat further constricts the dermal capillary network, which results in poor blood and lymph circulation. The tissues are starved of oxygen and nutrients and there is insufficient removal of waste products from the system as the connective tissue thickens and hardens and cellulite develops.

There are several factors that may be attributed to contribute to the development of cellulite. These are thought to include, amongst others:

genetics—some people are more hereditarily predisposed to acquire cellulite than others;

improper eating habits—certain ingredients such as alcohol, caffeine, and spicy foods produce an abundance of toxins that get trapped in the fatty tissue; also saturated fats clog the arteries preventing proper waste elimination;

bad dieting—during crash diets, the body "thinks" it is starving and tries to compensate by assisting in cellulite formation;

insufficient intake of water—water helps the waste system by flushing out toxins from the body;

smoking—smoking weakens the skin by constricting the capillaries and damaging connective tissue;

tension and stress -stress can cause connective tissue to seize up and block the tissue, thereby hindering proper waste elimination;

lack of physical exercise—exercise improves muscle tone and circulation, breaks blocked tissue and assists with purification;

medication—certain medicines such as diet pills, sleeping pills, and diuretics can disturb the purification system and other natural processes in the body; and hormonal problems—an improper balance between estrogen and progesterone levels influences the amount of fat stored or released by the body; also estrogen enlarges fat cells and leads to water retention that inhibits the body from flushing out toxins, as well as weakens the vertical connective tissue making it unable to contain the fat in organized chambers and allowing fat lobes to move up into the dermis layer.

In general, the ascribed causes of cellulite can be grouped into those that relate to weight problems, to poor circulation, and to insufficient drainage of waste elements in the bloodstream.

Cellulite is more common in females, partially perhaps because the fat storage chambers in male subcutaneous fat layers are arranged in smaller, diagonal units which store smaller quantities of fat and are less likely to contribute to cellulite formation. Another possible factor is hormones, which would explain why cellulite often appears in women during periods of hormonal change such as puberty, pregnancy, menopause, premenstrual syndrome, and during the initial months being on birth control pills. Hormone features explain why women tend to store fat in the lower halves of their body, and are more prone to poor circulation and fluid retention.

Cellulite poses primarily a cosmetic problem. The dimpled appearance of the skin is unattractive and undesirable. Nevertheless, people who display a lot of cellulite may be overweight and should be aware of the health risks associated with obesity, including heart disease and diabetes. Unlike fat, which acts as an insulator for the body and cushions the muscles, organs, and nerves, cellulite is thought to provide no substantial padding and is believed to be deprived of a beneficial purpose in modern life.

There are several existing approaches for the treatment of cellulite. These mainly include:

1. A surgical procedure where a small incision is made through which a tube is inserted and extraneous fat is pumped out.
2. A drug called Tomatil is injected into the subcutaneous tissues, and attempts to improve the blood flow within the capillaries between the fatty cells.
3. A device generates a vacuum that massages and kneads the skin and its subcutaneous layers, similar to "suction cup" treatments. The suction process results in an improvement in the blood flow and is supposed to rebuild the connecting tissues between the skin and the fatty layers, and to trigger the formation of collagen in the body.
4. Softening the skin via ultrasound waves.
5. Massaging the body by manual or mechanical means, the purpose of which is to improve blood flow and enhance purification and waste removal.
6. A massage technique based on suctioning and compressing at varying degrees. The suction and compression process is intended to improve blood flow and enhance purification and waste removal.
7. Creams and ointments that purportedly penetrate the skin layer and dissolve the fatty globules.
8. Capsules ingested orally that purportedly enhance purification and waste removal.

Many of these treatments have only a temporary effect. Most provide only minimal cellulite reduction. The current ultrasound treatments can also be painful and inefficient.

SUMMARY OF THE DISCLOSED TECHNIQUE

Accordingly, the disclosed technique seeks to provide a method and system that will reduce body perimeter, reduce or eliminate cellulite and fat from the body. There is thus provided a treatment system for reducing body perimeter at a region of treatment, including an ultrasound apparatus, wherein pressure exertion is applied to the region of treatment. The reduction of body perimeter comprises reducing or eliminating cellulite or reducing body fat, in humans, mammals, and animals. Possible treatment regions include legs, thighs, knees, buttocks, abdomen, stomach, and arms. The system can also be utilized to reduce or eliminate stretch marks, sagging skin, and skin affected by cellulite, render the general appearance of skin to look and feel smooth, or return the appearance of skin to a smooth state it looked like before sagging. The ultrasound apparatus is operated at a frequency ranging between 1 to 4 MHz, and at an intensity ranging between 1 to 3 W/cm$^2$, employed for 40 to 45 minutes per session. The range of 2.5 to 3.5 MHz is dedicated primarily for reduction and elimination of cellulite, preferably at about 3 MHz. The range of 0.9 to 1.6 MHz is dedicated primarily for reduction of body fat, preferably at about 1 MHz. The minimum suggested intensity is of 1.5 W/cm$^2$. According to another aspect of the disclosed technique, the ultrasound wavelength is varied over time. Preferably, the system includes pressure exertion apparatuses for applying the pressure exertion on the region of treatment simultaneously with the ultrasound apparatus up to 30 minutes after using the ultrasound apparatus. A pressure exertion apparatus may be applied on regions surrounding the region of treatment, such as above or below. The pressure exertion apparatus may feature the transducer head of the ultrasound apparatus, which may thus be used to provide a massaging action to the area of treatment. The massaging action may include moving the transducer head in ways such as small circular motions all the while keeping the wrist straight, and tilting and moving the wrist in different directions repetitively. The pressure exertion apparatus may include mechanical or manual massaging means, as weak as a massage given by bare hands. According to another feature of the disclosed technique, the pressure exertion apparatus includes an electrical stimulation apparatus capable of providing electrical stimulation to muscles surrounding the area of treatment, preferably operational in an intensity range between 5 to 90 mA, and in a frequency range between 5 to 150 Hz. Electrical stimulation techniques may include Interferential, Premodulated, Biophasica, IF Isoplanar (4 poles), IF Vectorial (4 poles), MF Stimulation, or combinations thereof. The stimulation techniques can be used in a pattern variation, wherein the pattern variation lasts varying times, and wherein the pattern variation consists of changing the stimulation technique during a treatment session. The frequency of operation of the electrical stimulation apparatus may be varied over time within the frequency range, such as by applying a specific frequency for a fixed amount of time before switching to another frequency, gradually changing the frequency from one extreme to another over various time durations, and only using extreme frequencies within the range intermittently. A rate of change of a variation of an operational wavelength of the ultrasound apparatus may be inversely proportional to a rate of change of a variation of the electrical stimulation apparatus operational frequency, a variation of an intensity of the electrical stimulation and a pattern variation of the electrical stimulation. The ultrasound apparatus may be used in conjunction with a gel rubbed on an area of treatment. The system may also include a camera, a processor, and a measuring apparatus with a pressure gauge.

According to the disclosed technique there is also provided a treatment method for reducing body perimeter including the procedures of applying ultrasound waves to an area of treatment, and exerting pressure on the area of treatment. The method may be used for reducing or eliminating cellulite, reducing body fat, for the body of humans, mammals, and animals, for legs, thighs, knees, buttocks, abdomen, stomach, and arms. The method may be used for reducing and eliminating post-pregnancy stretch marks, sagging skin, making the general appearance of skin look and feel smooth, returning the appearance of skin to the smooth state it looked like before sagging, having stretch marks on it, and being affected by cellulite.

A complementary measuring method is also provided, including standing a patient in an upright position, with the patient's arms down, measuring and recording the height of a region of treatment from the floor. The method further includes measuring the region of treatment using a measuring apparatus with a pressure gauge attached to it, measuring the region of treatment in a horizontal fashion, such that the measuring apparatus is placed around the region of treatment in parallel to the floor. The method further includes measuring the region of treatment using the measuring apparatus with the pressure gauge attached to it with a specific pressure exerted on the region of treatment and recording the measurement, and measuring the region of treatment a subsequent time using the measuring apparatus with the pressure gauge attached to it at the height of the region of treatment from the floor with the specific pressure exerted on the region of treatment, with the measuring apparatus being horizontal to the floor while measuring the region of treatment.

BRIEF DESCRIPTION OF THE DRAWINGS

The disclosed technique will be understood and appreciated more fully from the following detailed description taken in conjunction with the drawings in which.

DETAILED DESCRIPTION OF THE PREFERRED EMBODIMENTS

The following is a discussion of guiding principles for how the disclosed technique is effective in reducing body perimeter, in reducing or removing cellulite from the body, and in reducing fat from the body. It is noted that the disclosed technique was developed primarily for treating human beings, but it is also applicable to any mammal or other animal inflicted by cellulite or excessive fat.

Figure 1:
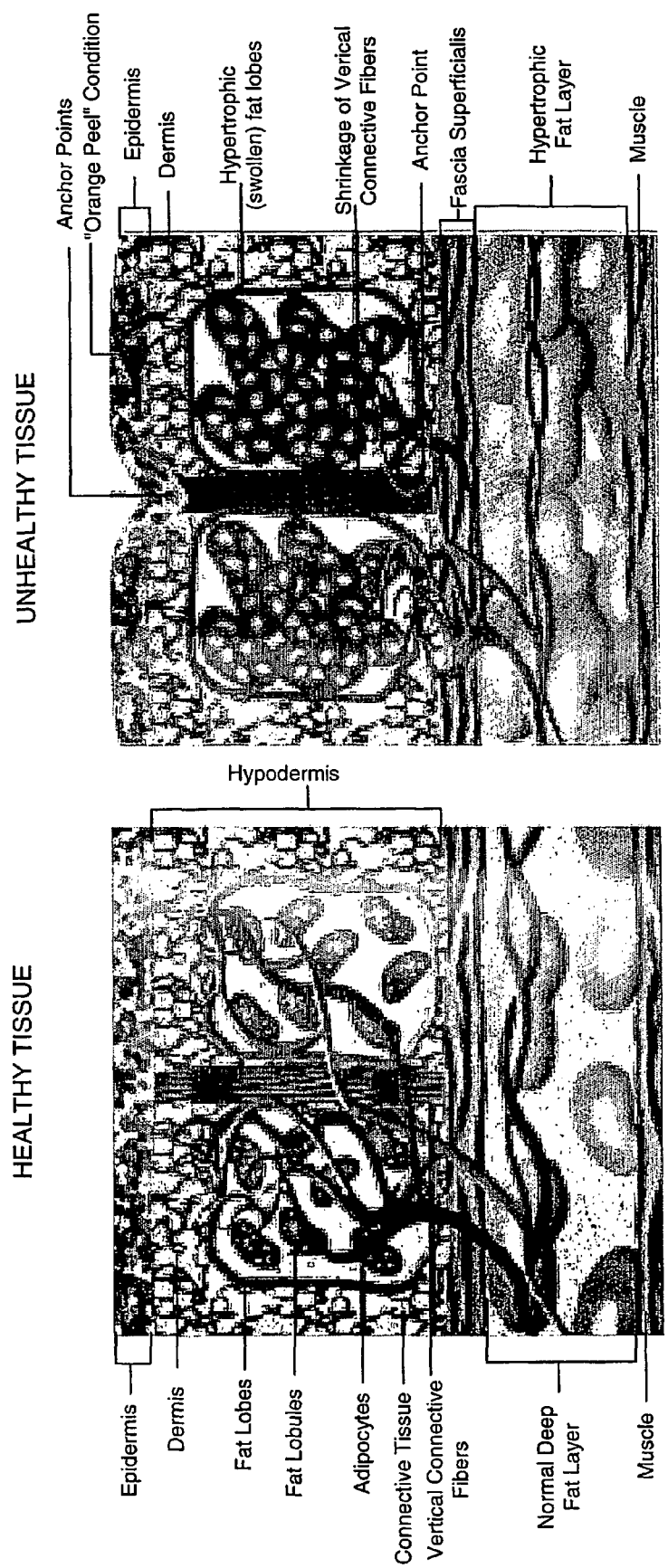
FIG. 1 is a schematic cross-section illustration of the skin structure and underlying layers in the human body.

Cellulite is located under the dermis and epidermis layers of the skin. It is characterized by swollen fatty lobules or globules filled with fat, fluids, and toxins, enclosed by the collagen fiber walls. These swollen fatty globules are arranged in several lobes or compartments separated from one another by collagen fibers, generating a pattern that resembles a cluster of grapes. It is to be noted that these globules and compartments can also be described as capsules or chambers, and these terms are used interchangeably herein. The formation of cellulite results from the gradual thickening of the subcutaneous fatty cells that capture fluids and toxins in the dermis and epidermis. In an absence-of-cellulite state, the blood supplies oxygen and nutrients to the tissues, while the lymphatic system removes waste products and extraneous fat. However in a cellulite state, due to the thickening of the fat into clumps, the arteries and capillaries become congested, as illustrated in the 'unhealthy tissue' drawing of FIG. 1. This congestion leads to a reduction in the rate of blood circulation. This in turn leads to a situation where the tissues receive less oxygen and nutrients, which results in a sharp decline in the waste removal and tissue regeneration processes. As a result of this progression, the body is unable to break down the accumulated compressed fat and to get rid of it. Therefore, it is a goal of the present technique to break down and dissolve cellulite fat through the collagen fibers which enclose it, allowing it to be drained by the lymphatic system. It is also desirable to accelerate blood circulation rate at the treated region, creating thereby a situation where the tissues receive increased oxygen and nutrients, which improves tissue regeneration and the drainage of extraneous fat. The disclosed technique constructively contributes to promote these goals.

It is conjectured that the disclosed technique embodies a mechanism by which the breakdown and dissolution of cellulite can be achieved through the application of ultrasound in a particular manner. It will be appreciated that the disclosed technique refers to the reduction of body perimeter in general, which may be attributed to the reduction or elimination of cellulite as well as the reduction of body fat. However, the disclosed technique may also be effective on other tissues, such as skin, and the like.

Figure 2:
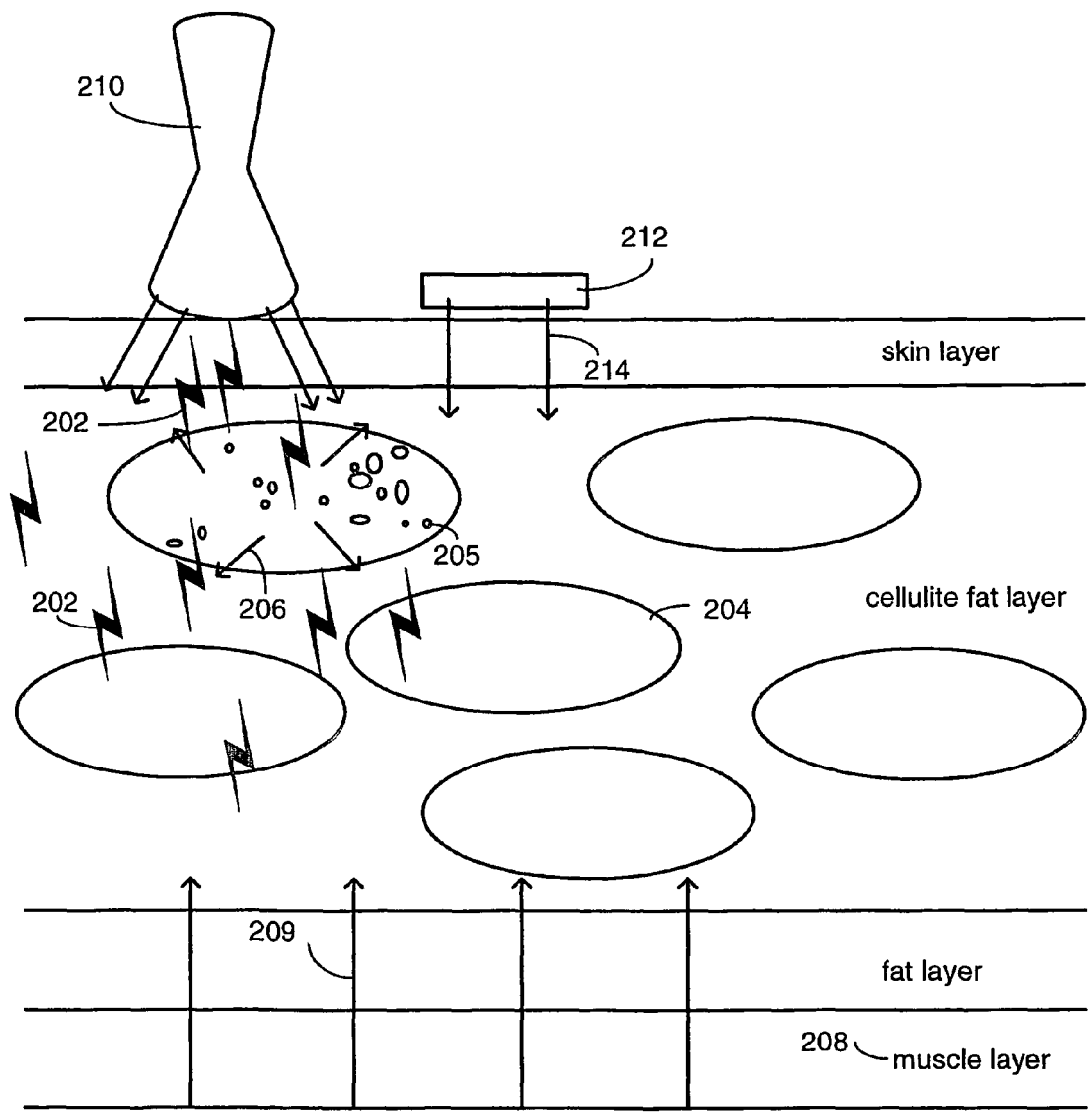
FIG. 2 is a schematic illustration of physical processes that occur during operation of the disclosed technique.

Reference is now made to FIG. 2, which is a schematic illustration of physical processes that occur during operation of the disclosed technique. Ultrasound waves 202 are very high frequency sound waves that generate heat and create changes in the density and pressure of the medium through which the waves pass. The ultrasound waves 202 are longitudinal waves made up of high pressure regions ("Compression") and low pressure regions ("Rarefaction"). When a wave strikes a material, the particles of that material begin to oscillate and gradually generate heat. Thus energy is transferred from the ultrasound wave into thermal energy of the impacted material.

One effect of ultrasound application to an impacted medium is micro-massage. Micro-massage refers to a massage-like process within the molecules of the impacted medium. When ultrasonic waves 202 pass through the interior of the fat capsules or chambers 204, waves 202 cause the fat molecules to vibrate. This vibration generates heat that can break down and dissolve the fat, which also endures compression within the enclosing capsules 204.

The ultrasound waves 202 can trigger an additional phenomenon called cavitation, whereby hydrogen bubbles 205 are formed as a result of the accumulation of dissolved gas within the medium of capsules' 204. When ultrasound waves 202 are applied at relatively high frequencies, the hydrogen bubbles 205 become unstable and burst quickly, releasing a large amount of energy. It is commonly recommended in the art to refrain from applying such high frequencies and to avoid cavitation, in fear of damaging healthy body tissue. However, by applying the present novel technique, it was found that cavitation has several, possibly relevant, consequences in the context of the disclosed technique. It was found that fatty clumps enclosed within the collagen fibers which heated up and at the same time broke down because of cavitation, also dissolved, and even dispersed. The dissolving and dispersing of fatty clumps enclosed within the collagen fibers can be attributed to cavitation. It is further conjectured that the burst hydrogen bubbles create a high pressure chamber within the collagen capsules 204, which causes cracks and tears to form in the collagen envelope of capsules 204. These cracks and tears appear to allow the dissolved fat molecules to be released out of the collagen walled capsules 204, as represented by arrows 206. Consequently, the dissolved fat can then be drained from the body by the lymphatic system.

Following extensive research, it was discovered that the release of fat molecules from the capsules 204 appears at certain frequencies and intensities of ultrasound waves 202. Conventional treatments operate at frequencies around 1 MHz and at intensities of up to 1.5-2.1 watts per square centimeter (W/cm$^2$) for a maximum duration of 10-15 minutes. At this range, it is conjectured that bubbles formed through cavitation are stable, the micro-massage effect takes place, and healthy tissue is not harmed. The disclosed technique emits ultrasound waves at a frequency of 1 to 4 MHz and at intensities varying from 1 to 3 W/cm$^2$ for a preferable duration of up to about 40-45 minutes. The recommended frequency for the reduction or elimination of cellulite fat is 3 MHz, though that number can be varied, preferably between 2.5-3.5 MHz, depending on the person being treated. The frequency should not be raised higher than a maximum of 4 MHz, around which point bubbles formed through cavitation are believed to become unstable. Lower frequencies should be used when treating cellulite in particularly fat organs to allow deeper penetration. A minimal intensity of 1.5 W/cm$^2$ is required to produce cavitation to an extent necessary for inducing fat dissolution and cracks in the collagen fibers. Frequencies below 3 MHz should be used to reduce non-cellulite fat. The recommended frequency for the reduction of non-cellulite fat is 1 MHz, though that number can be varied, preferably between 0.9-1.6 MHz, depending on the person being treated. If the patient experiences a burning sensation, then the intensity is reduced or the ultrasound transducer is moved more quickly in order to shorten exposure time to ultrasound waves.

While the ultrasound waves 202 are being emitted, the process can be dramatically enhanced by subjecting the treated region to a strong mechanical pressure. A mechanical pressure can be applied from above the skin or below the treated region, during the ultrasound emission or sufficiently promptly (without substantial delay) after the ultrasound emission. The pressure may be applied, for example, by a massage action, which may be comfortably applied by part of the ultrasound apparatus itself (with an operator or mechanical means exerting pressure), such as transducer 210, with its head in contact with the treated region. A kneading motion and the pressure applied to the treated region by the head of transducer 210 squeezes against the collagen capsules or chambers 204, which now contain dissolved fat. The internal pressure in these chambers 204 becomes greater than the external pressure (similar to a balloon). The pressure generated by the massage of the transducer 210 during the dissolving of the fat inside, compresses the chambers 204, squeezes the dissolved fat and extracts it out of the collagen capsules 204, through ruptures and cracks in the walls of the chambers 204. It is noted that the kneading action or the pressure exertion, according to the disclosed technique, deviates from the general practice of applying ultrasound waves. The general practice discourages any forceful contact between an ultrasound transducer and the skin.

According to another measure that can be applied to the treated region, this time from below, electrical stimulation using electrodes can be used to cause the muscles in muscle layer 208 to alternately contract and relax. Current is applied through the electrodes at frequencies ranging from 5-150 Hz and at intensities ranging from 5 to 90 mA, preferably with, but not limited to, Interferential, Premodulated and other techniques, further elaborated below. The rapid contraction-relaxation movement repetitively presses against the collagen structures 204 from below which house the dissolved fat, represented by pressure arrows 209, and squeezes the dissolved fat outside thereof in an extracting action. Electrical stimulation can be applied while the ultrasound waves are being emitted, thereby making the fat extraction process more effective as it also subjects the treated region to a strong mechanical pressure from below. In addition, application of pressure after exposure to ultrasound treatment is likewise effective for extracting fat, as the cracks and ruptures in the capsules already exist as long as the fat is still dissolved. This applies to the period of time starting immediately after the ultrasound treatment and for a while afterwards. It was found effective for at least half an hour after an intensive ultrasound treatment.

A further measure to exert pressure on the treated region is by a manual or mechanical external massage from above, such as by massaging means 212, as well as by bare hands. A most practical and simple massaging means is the mere massaging by the hands of a treating person. However, other mechanical massaging means are effectively applicable. The massage presses downwards, as represented by arrows 214, against the collagen structures 204 which house the dissolved fat, and thereby squeezes the dissolved fat outside of structures 204. Throughout the course of the process, a massage 212 also improves blood flow and operation of the lymphatic system. As with the electrical stimulation of the muscles, the massage can be applied effectively while the ultrasound treatment is provided or for a while thereafter.

The application of one or any combination of any of the four pressure increasing measures detailed above (micro-massage, ultrasound transducer kneading, electrical stimulation, and manual/mechanical massage), can exert sufficient and suitable pressure on the treated region from above and from below that contributes to an effective treatment. It was found that the more (and preferably all) of the measures that are applied, the more substantial and irrefutable reduction and eventual elimination of cellulite occurs, as well as the reduction of non-cellulite fat, and the reduction in body perimeter. The micro-massage is an outcome of the ultrasound application. The optional ultrasound transducer kneading, the electrical stimulation, and the manual/mechanical massage can be applied simultaneously with the ultrasound application, as well as for a while thereafter. It is conjectured that the exertion of pressure from above the treated region (by ultrasound transducer kneading and/or manual/mechanical massage) and from below the treated region (by electrical simulation) together aids most effectively in squeezing out the dissolved fats of structures 204.

In addition, an improvement in the circulatory system of the body is anticipated to result from the treatment. Due to the dissolution of the fat, the arteries and capillaries in the blood between cellulite capsules that were constricted before are now freed. The blood circulation is then accelerated, and the tissues receive more oxygen and nutrients. This in turn improves the purification process and tissue regeneration in the body. As a result, the blood system and lymphatic system return to their normal states. This development helps remove the extraneous fat from the body and makes the skin appear smoother. It will be appreciated that the effect of the disclosed technique is not necessarily limited to cellulite and non-cellulite fat and may well be effective in reducing body contour and smoothing skin due to its effect with other tissue such as the skin, perhaps even muscles, and the like.

According to another aspect of the disclosed technique, a gel that is rubbed onto the skin is preferably water-based to conform to the ultrasound conductive medium required by ultrasound applications. Preferable gels can include ingredients such as: hydroxyl acids, plant extracts, wheat proteins, macadamia oil, chamomile, zinc, salicylic acid, and caffeine. The gel has several purposes. Firstly, it effectively conducts the ultrasonic waves between the ultrasound transducer and the skin tissues. In addition, the gel lubricates the skin and prevents friction and scrapes to the skin, especially in circumstances where the head of the ultrasound transducer is strongly rubbed in a kneading or similar motion to provide a massage to the treated region. Also, drugs and active ingredients, if added to the gel, are absorbed into the epidermis layer more effectively because of the ultrasound waves, the heated fluids and tissue material, and the appearance of ruptures or cracks in the treated tissue. This absorption is further enhanced by the ultrasound transducer head forcefully rubbing the gel against the skin. These drugs or active ingredients that are absorbed can catalyze blood flow, and transmit into the skin surface and perhaps beneath thereof the minerals and nutrients the skin lacks due to insufficient blood flow and poor purification at the cellulite inflicted region. The application of the nutrients can also substantially improve the skin appearance. Throughout the course of the process, the massage action that rubs the gel into the skin improves blood flow and operation of the lymphatic system.

In summary, efficient removal of the dissolved cellulite and non-cellulite fat can be achieved by a combination of factors. The ultrasound waves result in micro-massage and in cavitation. This causes an increase in the internal pressure of fat structures 204 and in heat in the cellulite fat layer and/or the fat layer, as well as the development of hydrogen bubbles. The pressure increase pushes the dissolved fat against the collagen walls and the fat molecules are diffused through the collagen membrane that was cracked from the burst hydrogen bubbles. Different measures can augment fat extraction. Measures that are immediately available include: micro-massage, ultrasound transducer kneading massage, manual or mechanical massaging action, and electrical stimulation.

Figure 3:
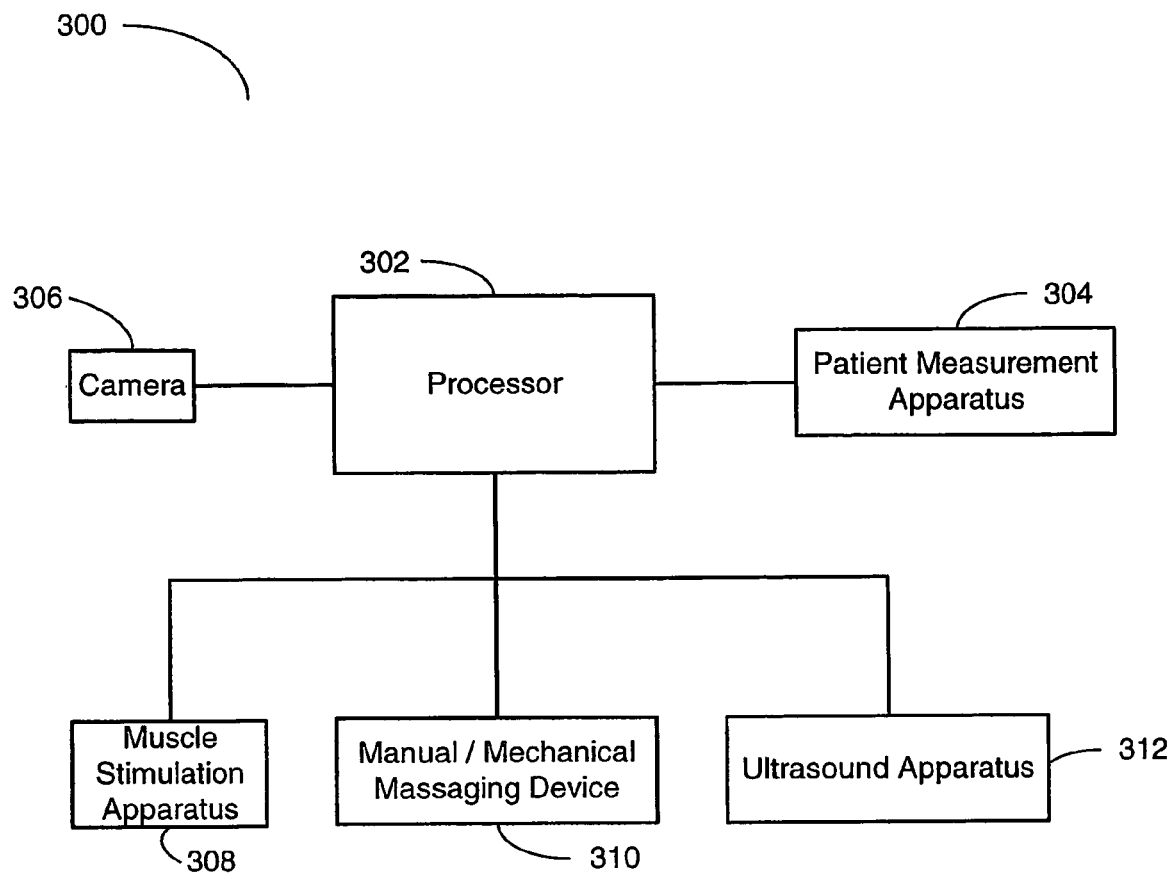
FIG. 3 is a schematic illustration of a system, constructed and operative in accordance with an embodiment of the disclosed technique.

Reference is now made to FIG. 3, which is a schematic illustration of a system, generally referenced 300, constructed and operative in accordance with an embodiment of the disclosed technique. System 300 includes a computer or processor 302, patient measurement apparatus 304, a camera 306, muscle stimulation apparatus 308, a manual/mechanical massaging device 310, and an ultrasound apparatus 312. Processor 302 is coupled with and controls patient measurement equipment 304, camera 306, muscle stimulation apparatus 308, manual/mechanical massaging device 310, and ultrasound apparatus 312. Patient measurement apparatus 304 measures physical parameters of the patient such as: weight, interior or exterior contour of a body part, body fat ratio, and the like. These measurements are taken before, during and/or after the treatment. Processor 302 records these measurements or provides it to an external memory (not shown). Camera 306 records the treatment process; the recording can be stored with processor 302 or in an external memory, to provide subsequent evidence, additional or alternative measuring means, and to assist for future treatment improvements. Muscle stimulation apparatus 308 includes electrodes that attach to the patient to provide electrical stimulation of the muscles of the patient. Manual/mechanical massaging device 310 massages the patient at the cellulite inflicted treatment region or the fat reduction region. Ultrasound apparatus 312, typically consisting of a signal generator unit and a transducer unit, transmits ultrasound waves at the cellulite inflicted region or the fat reduction region. Preferably, therewith, ultrasound apparatus 312 is designed to allow simultaneous kneading of the skin of the patient. It will be appreciated that in this embodiment, measurement apparatus 304, camera 306, and massaging device 310 are optional. Also processor 302 can be eliminated if ultrasound apparatus 312 and muscle stimulation apparatus 308 include or are supported by the necessary means to provide the relevant power, intensities and frequencies required for their operation. Massaging device 310 can be eliminated when manual massaging is applied. Muscle stimulation apparatus 308 is preferably not eliminated, unless substantial pressurizing means (such as device 310 or a massaging head of ultrasound apparatus 312) can provide the sufficient pressure to extract the cellulite fat and/or the non-cellulite fat.

Figure 4:
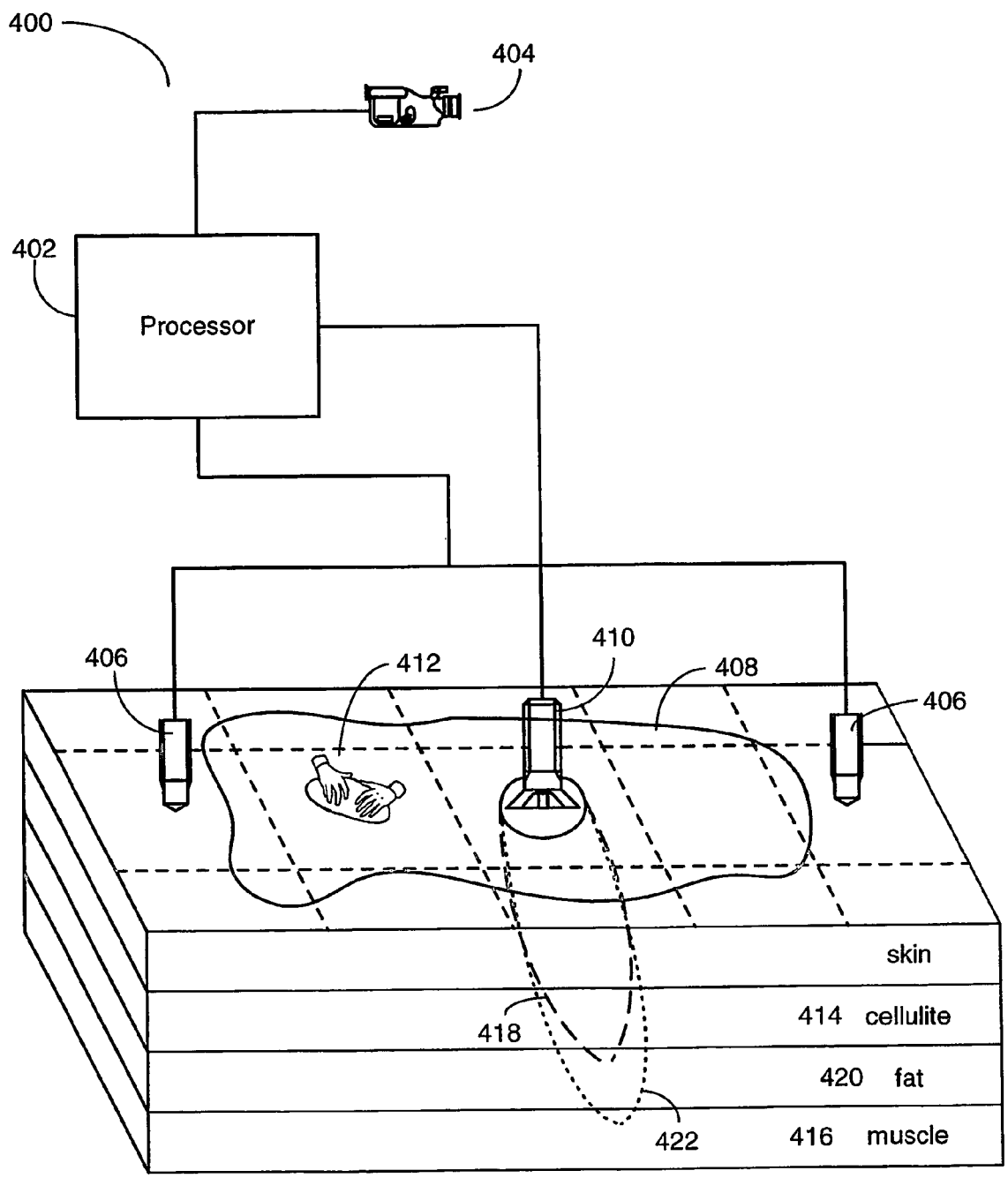
FIG. 4 is a schematic illustration of a system, constructed and operative in accordance with another embodiment of the disclosed technique.

Reference is now made to FIG. 4, which is a schematic illustration of a system, generally referenced 400, constructed and operative in accordance with another embodiment of the disclosed technique. A processor 402 controls the activity of a camera 404, electrodes 406, and an ultrasound transducer 410. Camera 404 films the treatment process, to provide subsequent evidence, for measurement, and to assist for future treatment improvements. Electrodes 406 attach to the patient to provide electrical stimulation of the muscles of the patient. Gel 408 is applied to the patient at the cellulite inflicted treatment region or the fat reduction region. Massage of the patient at the treatment region is represented by hands 412, and can be substituted or assisted by a massaging apparatus (not shown). Ultrasound transducer 410 simultaneously kneads the skin of the patient and transmits ultrasound waves at the treatment region. It should be noted that the ultrasound waves penetrate the skin surface until the cellulite fat layer 414, where they proceed to affect that region. The ultrasound waves fade as they penetrate deeper into the body of the patient, and their intensity and frequency is selected to prevent reaching the layer of muscle tissues 416 further below, which would be painful and may perhaps harm these healthy tissues. A typical cross-section of effective ultrasound penetration is represented by perforated line 418, demonstrating its covering of the entire cellulite layer 414, with possible penetration into the fat layer 420. If reduction of fat in fat layer 420 is sought, the penetration represented by perforated line 418 can be extended to cover most or all of fat layer 420. If the effective ultrasound penetration reaches the muscle layer 416, as represented by dotted line 422, this can impose pain in the muscles and perhaps even damage thereto. Further aspects of the embodiment shown in FIG. 4 are analogous to the aspects described in reference to FIG. 3 and are therefore not elaborated.

Figure 5:
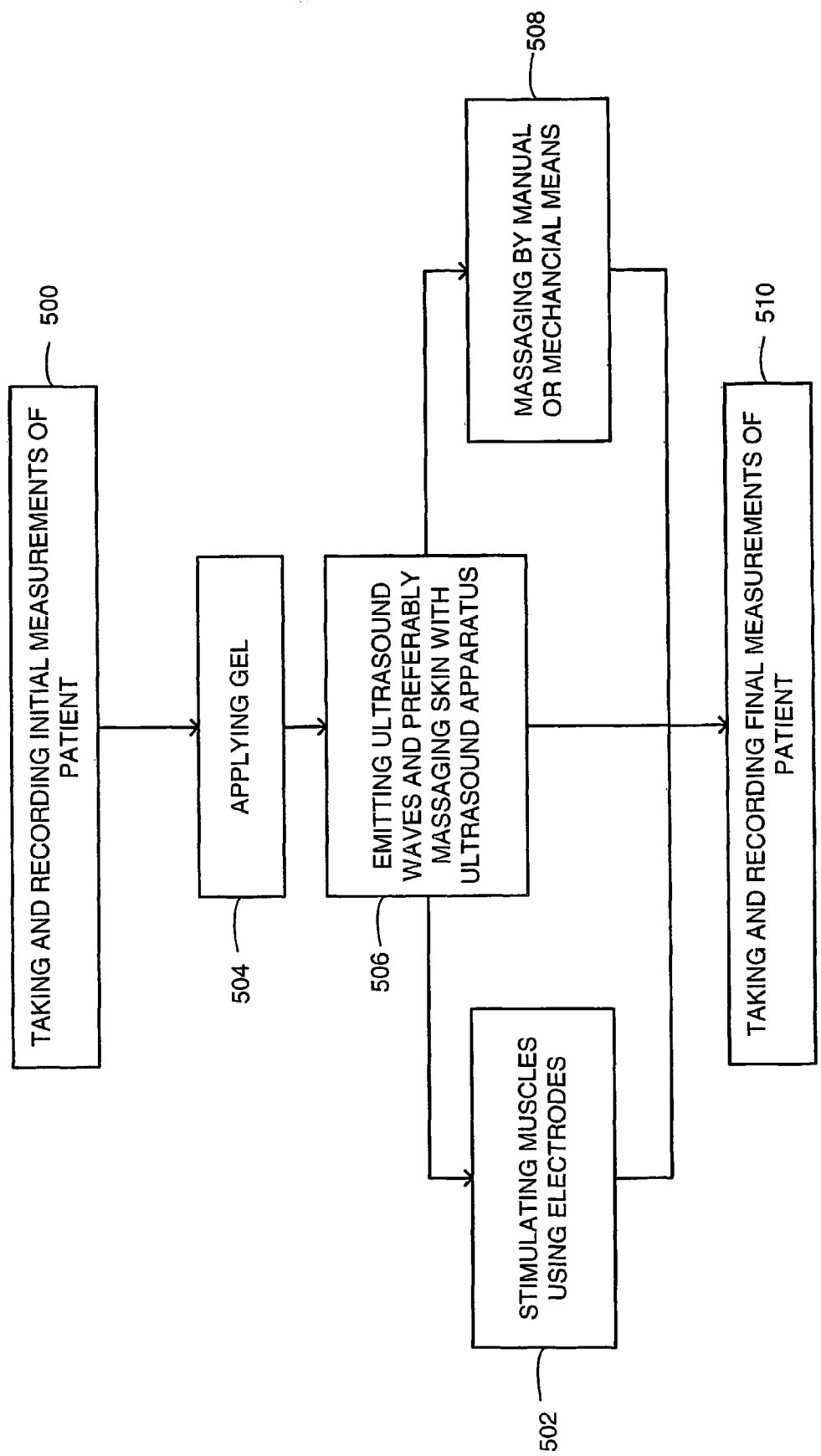
FIG. 5 is a schematic illustration of a method for treating cellulite and/or non-cellulite fat, operative in accordance with an embodiment of the disclosed technique.

Reference is now made to FIG. 5, which is a schematic illustration of a method for treating cellulite and/or non-cellulite fat, operative in accordance with an embodiment of the disclosed technique. In procedure 500, the initial measurements of the patient are taken and recorded. First, the patient is weighed before each session, and his/her weight is recorded. The patient is asked to maintain the same approximate weight over the duration of the treatment, or in other words, not to go on a diet or any other means that would reduce the patient's body weight, in order to prove that the eventual reduction of body organ perimeter results from the ultrasound treatment rather than from mere weight loss. Normally, a loss of 1-4 kg, depending on the size and fatness of the patient, will not be noticed in the measurements. The measurements of the patient are taken as follows. Once the region to be treated is decided upon, the borders of the area are indicated with an erasable marker, as illustrated for example by the perforated straight lines on the skin in FIG. 4. This region is divided into separate sections at intervals of 5 cm, and each section is numbered and marked off with a horizontal line. This is done to facilitate treatment so the person giving the treatment knows which regions have been treated so far. One simple and accurate method for repeated measurements can involve standing the patient and measuring distances from each region to the ground, with simple metering means. The interior contour of the treated organ, for example thigh, leg, arm, and the like, is measured at each section. Then the overall perimeter of the body at each section is measured as best as possible. For example, this can involve measuring the complete contour of the waist or the contour of two thighs when the legs are pressed together.

Figure 7:
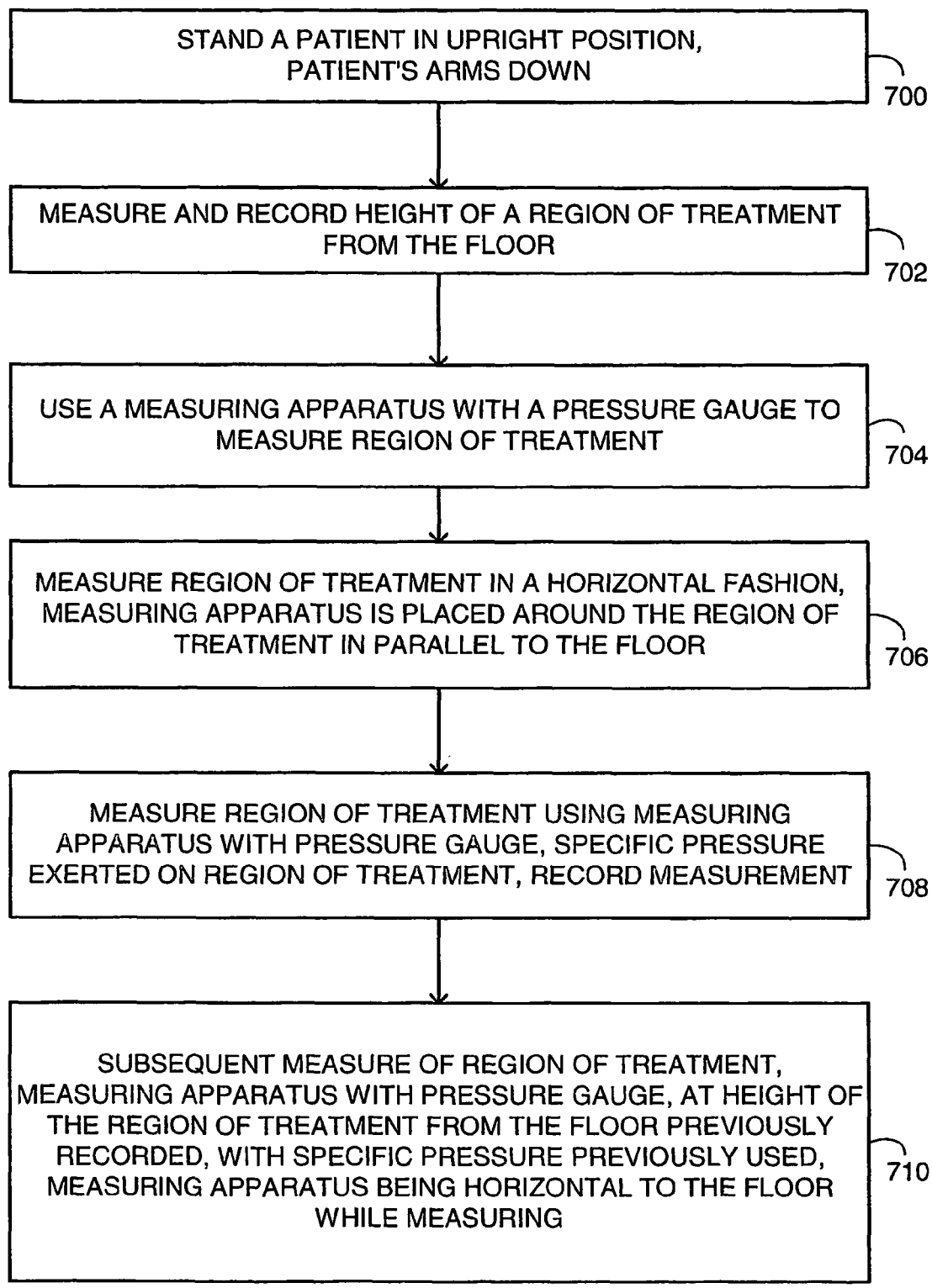
FIG. 7 is a schematic illustration of a method for accurately and repetitively measuring the regions of treatment of a patient undergoing the ultrasound treatment of the disclosed technique used in conjunction with an embodiment of the disclosed technique.

Reference is now made to FIG. 7, which is a schematic illustration of a method for accurately and repetitively measuring the regions of treatment of a patient undergoing the ultrasound treatment of the disclosed technique used in conjunction with an embodiment of the disclosed technique. In procedure 700, the patient is stood in an upright position, with the patient's arms down. In procedure 702, the height of the region of treatment is then measured from the floor and recorded. This is done so that repeated measurements of the same area can be done accurately as a person's height will not change due to the treatment. In procedure 704, a measuring apparatus with a pressure gauge attached to it is used to measure the region of treatment. In procedure 706, the region of treatment is measured in a horizontal fashion, meaning the measuring apparatus is placed around the region of treatment such that it is parallel to the floor. In procedure 708, the region of treatment is measured with a specific pressure exerted on it and the measured value is recorded. In procedure 710, the same specific pressure is used at the recorded height of the region of treatment each time a measurement is made of the region of treatment. This is to guarantee that the measurement is accurate and does not reflect a change in pressure of the measuring apparatus around the region of treatment or a change in the height of the region of treatment being measured. In reference to FIG. 3, patient measurement apparatus 304 is utilized for measuring the patient's physical parameters before, during and after the treatment. After all the measurements have been taken, the patient is instructed to lie down on the bed.

Referring back to FIG. 5, in procedure 502, the muscles of the patient are stimulated using electrodes. In reference to FIG. 4, electrodes 406 are attached to the patient's body at the treated region. Electrodes are attached to the skin, with the aid of attaching means such as adhesive patches, at the beginning and end of the muscle fibers that cross the treated area. Current is applied through the electrodes at frequencies ranging from 5-150 Hz to stimulate intermittent contractions of the muscles. These contractions create a tense bedding of muscle against the cellulite and/or fat layer. Such tense bedding provides a counter wall for the pressing of the cellulite tissue and/or fat tissue being treated. The trembling motion of the muscles applies periodic squeezing to the cellulite tissue and/or fat tissue, especially if external pressure from above is mechanically applied to the region as well. It is believed that periodic application of pressure pulses with alternating relief intermissions is preferable over constant pressure application with respect to the tenability of living organic tissue, especially in circumstances of force accompanying an aggressive treatment.

The electrical stimulation of the muscles is preferably done with Interferential, Premodulated, Biophasica, IF Isoplanar (4 poles), IF Vectorial (4 poles), MF stimulation, and the like techniques, as known in the art of electrode stimulation. The electrical stimulation is applied at intensities ranging from 5 to 90 mA. Electrode stimulation is known in the field of muscle buildup treatment 1o as is found in the fields of physiotherapy and sports. The Interferential technique uses two alternating currents originating at different channels, each at slightly different carrier frequencies. These currents will meet at the treatment area and create interference (constructive or destructive), producing a resultant beat frequency. The beat frequency is the difference between the actual frequencies provided by each pair. For example, a frequency of 100 Hz is yielded by 3,900 Hz in one electrode pair and 4,000 Hz in the other electrode pair. Accordingly, the resultant wave is a 3,900-4,000 Hz carrier wave modulated at an envelope amplitude frequency of 100 Hz. The dominant carrier frequency depends on the geometrical locations of the electrodes. Interferential stimulation is almost exclusively delivered with the quad-polar technique, in which four independent pads are placed in such a way as to achieve the desired effect. Typically, two pairs of electrodes are arranged around the treatment area, with each pair perpendicular to the other. Bipolar electrode placement may also be used, where the interference occurs within the generator rather than within the tissues, thereby requiring only one pair of electrodes to be used. The Premodulated technique involves superimposing a signal with the effective frequency onto a continuously transmitted carrier wave, for instance, a 4000 Hz carrier wave modulated at an envelope amplitude frequency of 100 Hz. The modulation occurs before application thereof to a single pair of electrodes, rendering another pair of electrodes unnecessary. The electrical stimulation of muscles during treatment does not need to be done with one particular type of electrical stimulation technique. Multiple techniques can be used in various combinations in terms of which techniques are used, in what order they are used, and how long they are used before another technique is used. For example, electrical stimulation during treatment may involve using the IF Vectorial technique first for 10 minutes, then switching to the Interferential technique for 5 minutes, then to the Premodulated technique for an additional 5 minutes, then to the Biophasica technique for another 10 minutes, then cycling back through this process again. According to another example, electrical stimulation during treatment may involve using the Interferential technique first for 8 minutes, then switching to the IF Vectorial technique for 2-3 minutes, then switching to the Premodulated technique for 6 minutes, then to the Biophasica technique for 7 minutes, then switching to the MF stimulation for 5-10 minutes then cycling back through this process again. It was found that the Interferential, IF Isoplanar, IF Vectorial, and Premodulated techniques work best, with the IF Vectorial technique being the most effective in terms of stimulating muscles to contract to aid in squeezing out fat in the cellulite and fat layers. While each technique is applied the carrier wave frequency is preferably changed (hopped) at least once, thus avoiding adaptation of the living body to the stimulation (thereby ceasing to react with intermittent contractions), and saving the need to increase the stimulation intensity. For example, while each technique is applied, the carrier wave may be hopped from a 4,000 Hz carrier wave to a 2,400-2,500 Hz carrier wave. Similarly, the envelope or beat frequency (where relevant) is changed gradually or hopped between selected frequencies.

During the initial treatment session, it is preferable to use lower intensities, starting with 3-5 mA, as a high current intensity can be agitating and can frighten an inexperienced patient. In more advanced treatments, it is possible to apply the more effective higher intensities in the range of 5-90 mA. The effective frequencies are between 5-150 Hz. It is noted that in using the different electrical stimulation techniques mentioned above, for example Interferential, Premodulated, and the like, the muscles do not react (with intermittent contractions) to frequencies above 250 Hz. At higher frequencies the vibrations are so frequent that the muscles can remain constantly tense. At lower frequencies, the vibrations are slower but much stronger. Since the muscle adapts to a specific frequency, it is therefore advisable to alter the frequency of the electrical stimulation throughout the duration of the treatment, and even during a specific stimulation technique. Apart from using a specific frequency and/or altering the frequency manually or arbitrarily, four other patterns for altering frequency are common: (1) applying a specific frequency for a fixed amount of time before switching to another frequency; (2) gradual change, such as going from 5 to 150 Hz and back (such as in a sinusoidal cycle); (3) like (2), but remaining for a longer duration (such as 1 sec) at the extreme levels; (4) only the extreme frequencies are used, intermittently. Other patterns for altering the frequency may also be used.

In procedure 504, gel is applied to the region of treatment. In reference to FIG. 4, gel 408 is applied to the skin at the treated region. Referring back to FIG. 5, the gel improves non-abrasive contact between the ultrasound transducer and the skin. The gel is also designed to provide for good conduction and smooth penetration of the ultrasound waves to the underlying tissues. The gel may include drugs and active ingredients that are absorbed into the skin surface. These drugs and active ingredients may catalyze blood circulation and may replenish the skin with minerals and nutrients lacking due to insufficient blood flow and poor purification at the cellulite inflicted region. Further effects of gel application are elaborated with respect to FIG. 4.

In procedure 506, an ultrasound apparatus emits ultrasound waves and preferably also massages the skin. In reference to FIG. 4, ultrasound transducer 410 is utilized for transmitting ultrasound waves and preferably for kneading the treated region. Referring back to FIG. 5, the ultrasound transducer is applied to the body at the marked off region. The ultrasound apparatus emits ultrasonic waves at a frequency of 1 to 3.5 (or 4) MHz and at intensities varying from 1 to 3 W/cm$^2$. A minimal intensity of 1.5 W/cm$^2$ is required to produce cavitation necessary for inducing both fat dissolution and cracks in the collagen fibers. The frequency as well as the wavelength of the ultrasound apparatus can be changed over the course of the treatment. A change in wavelength will allow different types of fat located at different depths in a patient to be targeted for reduction and elimination. Shorter wavelengths need to be used to reach the shallower cellulite fat layer whereas longer wavelengths need to be used to reach the deeper fat layer. In terms of varying the wavelength with regard to the type of fat being targeted, the treatment should consist of first treating one type of fat and only then moving on to a different type of fat. In other words, for example, first the cellulite fat should be treated and then the non-cellulite fat should be treated, or vice-versa. A change in frequency over the course of treatment appears to be effective in reducing and eliminating cellulite and fat and can also affect a patient's pain level. Therefore, the frequency may have to be altered within a desired range if a patient experiences pain at a particular frequency in the range.

Figure 6A:
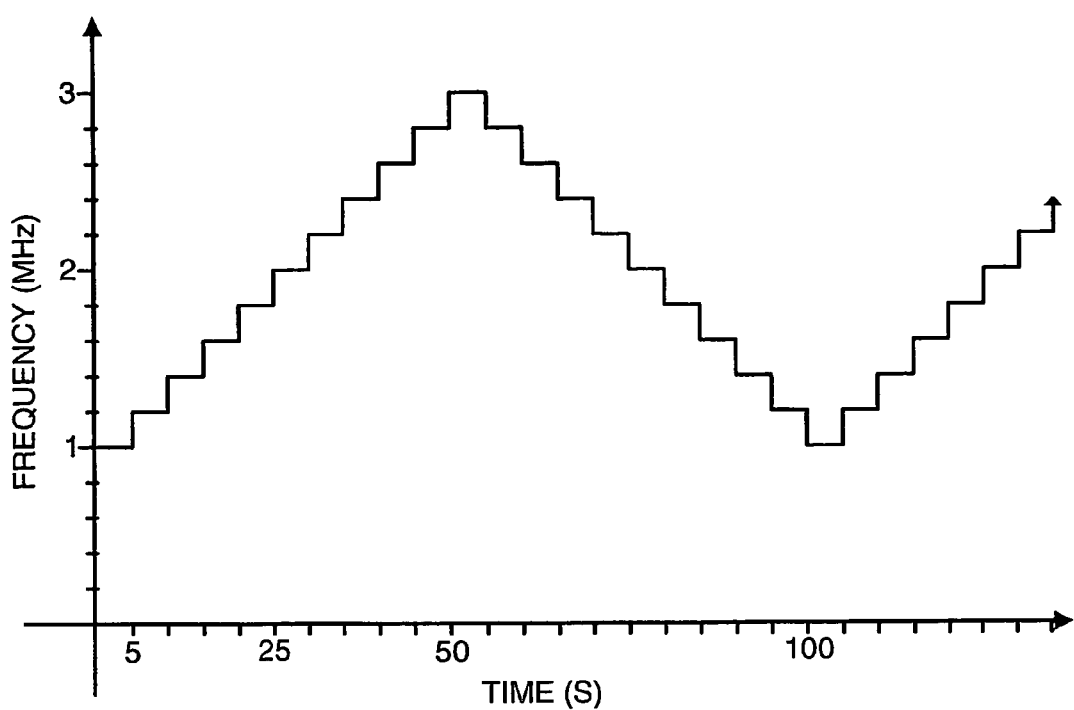
FIGS. 6A and 6B are graphs depicting examples of the variation of ultrasound wave frequency as a function of time used in conjunction with an embodiment of the disclosed technique.
Figure 6B:
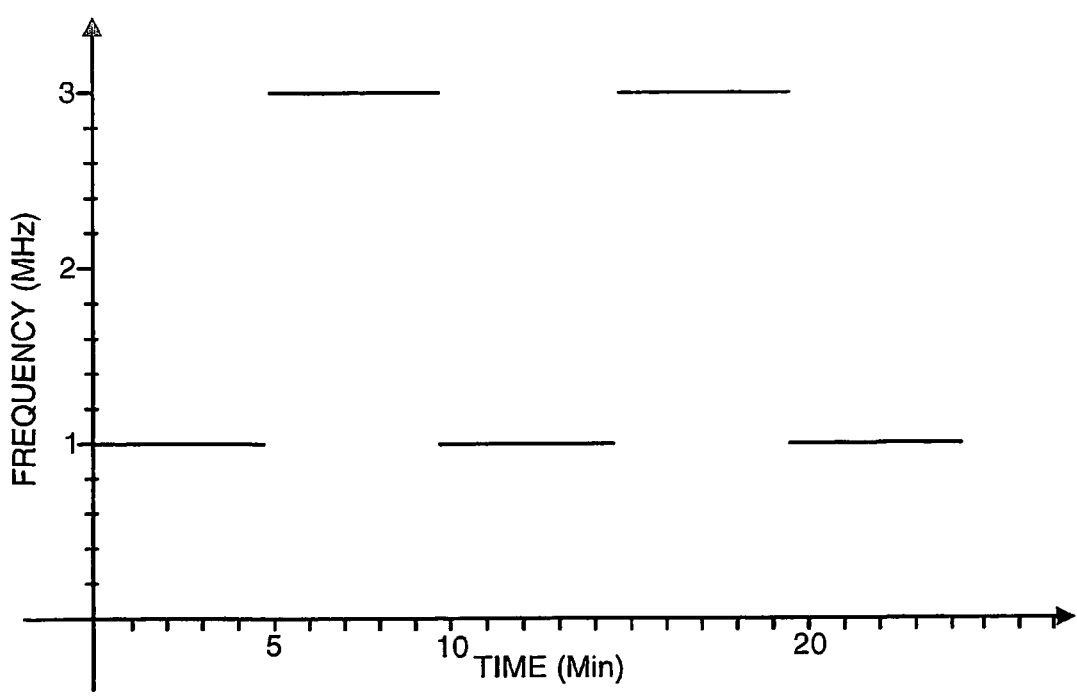

Reference is now made to FIGS. 6A and 6B which are graphs depicting examples of the variation of ultrasound wave frequency as a function of time used in conjunction with an embodiment of the disclosed technique. With reference to FIGS. 6A and 6B, two possible ways of altering the frequency of the ultrasound waves emitted over the course of time of the treatment are shown. For example, referring to FIG. 6A, the frequency can be altered over the course of the treatment from 1 MHz to 3 MHz and back again to 1 MHz, cyclically, at steps of 200 KHz lasting 5 seconds. The steps can also last a shorter or longer time period, for example 3 seconds or 10 seconds, and can be larger or smaller in step size, for example 100 KHz or 500 KHz. Referring to FIG. 6B, the frequency can also be altered sharply, in a stepwise manner, between 1 MHz and 3 MHz and back again to 1 MHz, cyclically, where a given frequency is applied for 5 minutes. The duration of time a particular frequency is applied can also last a shorter or longer time period, for example 3 minutes, 10 minutes, or 20 minutes. The frequency should not be raised higher than 4 MHz, as the results obtained from such high frequencies are not optimal.

Referring back to FIG. 5, the treated region of the skin, which is preferably smeared with a gel in procedure 504, is preferably subjected to the ultrasound treatment at the same time as electrode stimulation triggers the intermittent contractions of the muscle fibers in procedure 502, in order to increase the extraction of fat from the capsules and from the fat layer. However, procedure 502 can be performed after procedure 506 or both during and after procedure 506. Whether procedure 502 is performed after procedure 506 or both during and after procedure 506, if the frequency or intensity of the electrical stimulation of procedure 502 is varied rapidly, it is then suggested that the frequency or wavelength of ultrasound wave production of procedure 506 be varied slowly; and vice-versa, if the frequency or intensity of the electrical stimulation of procedure 502 is varied slowly, it is then suggested that the frequency or wavelength of ultrasound wave production of procedure 506 be varied rapidly. In other words, it is suggested that the rate of varying the parameters related to electrical stimulation of procedure 502 (frequency and intensity) should be inversely proportional to the rate of varying the parameters related to ultrasound wave production of procedure 506 (frequency and wavelength). However, if desired, the rate of varying the parameters of both (electrical stimulation and ultrasound), can be proportional and even identical.

The ultrasound transducer is moved slowly and gradually across the entire length and width of the region, all the while preferably executing small circular massage motions with the arm, all the while keeping the wrist straight. The ultrasound transducer is forcefully applied to the patient's body to generate substantial pressure. The ultrasound apparatus is preferably designed to allow both the forceful massage action and the penetration of ultrasound waves into the body. The changing force of the massaging action, which provides for periodic relief intermissions between the presses, is believed to contribute to the tenability of the organic tissue to an aggressive treatment. The ultrasound transducer can be also tilted in all directions (left, right, front and back) over the course of the massaging. This is achieved by tilting and moving the wrist in different directions repetitively, for example left-right-left, front-back-front, and left-front-right-back (circular motion using the wrist as opposed to circular motion using the arm). This way, the ultrasound waves penetrate deeper into the body of the patient, as the surface area of the head in contact with the skin is made smaller by the tilting. The massaging motion in general, and in particular that of the ultrasound transducer, is believed to help squeeze fat out of the cellulite fat layer and the fat layer. Therefore, the massaging motion does not need to be restricted to only one particular way. For example, small circular massage motions can be interspersed with left-right-left tilting massage motions, or any combination of the above mentioned massage techniques, or any other massage techniques.

In procedure 508, a massage is performed by manual or mechanical means. Preferably, this massage is applied to the treated area concurrently with the electrode stimulation (procedure 502) and the ultrasound application (procedure 506), but can also be applied after the ultrasound treatment in procedure 506. The intensity of the massage is dependent on the amount of cellulite (or fat) that is desired to be removed. More cellulite (or fat) present means a more intense massage is needed. It was found that it is most advisable to simultaneously apply the massaging action to the very same area subjected to the ultrasonic waves for achieving optimal effect. It is believed that the ultrasound softens the cellulite (or fat) tissue and allows the fat squeezing action achieved by the massaging to take place. An ultrasonic apparatus, such as one including a transducer head designed for both functions of ultrasonic transmission and massaging or pressure application, is a successful tool for achieving this goal.

The duration of the aforementioned treatment preferably varies from 30 to 45 minutes. Several treatments may be required to achieve satisfactory results. In summary, the treatment is a combination of several elements: application of a gel, application of ultrasound waves, ultrasound transducer kneading, electrode stimulation of the muscles, and manual or mechanical massage.

If procedures 502 or 508 are carried out after the ultrasound treatment in procedure 504, they are preferably carried out simultaneously, irrespective of the fact that any of procedures 502 and/or procedure 508 was already applied or not applied also during the ultrasound treatment of procedure 504. A post-ultrasound massage (procedure 508) or muscle stimulation (procedure 502) or the preferable combined massage and muscle stimulation in a post-ultrasound stage, requires 20-30 minutes. Further preferably, massage (procedure 508) or muscle stimulation (procedure 502) is carried out both during and after the ultrasound treatment of procedure 506. Most preferably, both the massage (procedure 508) and the muscle stimulation (procedure 502) are applied together both during and after the ultrasound treatment of procedure 506. In reference to the time consumed, the 20-30 minutes of post-ultrasound stage (procedures 502 and 508) follows the initial 45 minutes stage devoted to a combined ultrasound, massage and stimulation stage (procedures 502, 506 and 508).

In procedure 510, the final measurements of the patient are taken and recorded using any of the measuring techniques described above. A final measurement is carried out after the completed treatment to determine how much body contour or organ perimeter was reduced in the patient.

The above mentioned systems and method, described and shown in FIGS. 2 to 6B, are not only effective in reducing or elimination cellulite fat, and in reducing fat in the fat layer, but have been found effective in other areas. The above mentioned systems and methods have been found to work for reducing cellulite and non-cellulite fat in the stomach region of a patient. For treatment of the stomach region, the ultrasound waves used for treatment should have an optimal frequency of 1 MHz for the reduction of fat in the stomach area, and 3 MHz for the reduction of cellulite fat in the stomach area, as mentioned above. With regards to treating the stomach region, the above mentioned systems and method have also been found to be effective in reducing and even eliminating the appearance of post-pregnancy stretch marks on the stomachs and mid-sections of women. In about half the cases the stretch marks were visibly reduced, and in some cases completely disappeared. It is noted that no other technique substantially reduces or eliminates stretch marks on the stomach that result from pregnancy to a similar extent. The above mentioned systems and method have also further been found effective in reducing and eliminating sagging upper arm skin, usually found in older women. Sagging upper arm skin refers to the skin located on the underside of the upper arm, positioned between the elbow and the armpit. The above mentioned systems and method may also be effective in reducing or eliminating sagging skin in other parts of the body. It is noted that current methods for reducing sagging skin using techniques of plastic surgery do not give seamless results, whereby there is no evidence of some technique performed on the sagging skin. Furthermore, the above mentioned systems and method were also found effective in making the general appearance of skin, whether it be sagging skin, skin having stretch marks, or skin showing varying degrees of cellulite, look and feel smooth, returning the appearance of the skin to the smooth state it looked like before sagging, having stretch marks on it, or being affected by cellulite.

It will be appreciated by persons skilled in the art that the disclosed technique is not limited to what has been particularly shown and described hereinabove. Rather the scope of the disclosed technique is defined only by the claims, which follow.

The invention claimed is:

1. A treatment system for reducing body perimeter at a region of treatment, said treatment system comprising:
an ultrasound apparatus, for transmitting ultrasound waves to said region of treatment, at an intensity of between 1.5 W/cm$^2$ to 3 W/cm$^2$, wherein the operational frequency of said ultrasound apparatus is varied over time during a treatment session; and
an electrical stimulation apparatus, for applying electrical stimulation to said region of treatment simultaneously with said transmission of ultrasound waves, wherein said electrical stimulation comprises interferential stimulation, wherein the operational frequency of said electrical stimulation apparatus is varied over time during the treatment session;
wherein the operational frequency of the ultrasound apparatus is varied at a rate that is inversely proportional to a rate at which the operational frequency of said electrical stimulation apparatus is varied during the same treatment session.

2. The treatment system of claim 1, wherein said reduction of body perimeter comprises reducing or eliminating cellulite.

3. The treatment system of claim 1, wherein said reduction of body perimeter comprises reducing body fat.

4. The treatment system of claim 1, wherein said reduction of body perimeter comprises reduction of body perimeter in a human or an animal.

5. The treatment system of claim 1, wherein said reduction of body perimeter comprises reduction of body perimeter in regions of the body selected from the list consisting of: legs, thighs, knees, buttocks, abdomen, and arms.

6. The treatment system of claim 1, wherein said system is utilized to reduce or eliminate stretch marks.

7. The treatment system of claim 6, wherein said stretch marks are located on the abdomen and mid-sections of women.

8. The treatment system of claim 1, wherein said system is utilized to reduce or eliminate at least one selected from the list consisting of: sagging skin, skin having stretch marks on it, and skin affected by cellulite.

9. The treatment system of claim 8, wherein said sagging skin comprises upper arm skin.

10. The treatment system of claim 8, wherein said system is utilized to render the general appearance of said sagging skin to look and feel smooth, or to return said appearance of said sagging skin to the state it appeared before sagging.

11. The treatment system of claim 1, wherein said ultrasound apparatus is operational at a frequency ranging between 1 to 4 MHz.

12. The treatment system of claim 1, wherein said ultrasound apparatus is operational for a duration of 40 to 45 minutes per session.

13. The treatment system of claim 1, wherein said ultrasound apparatus is operational at a frequency of approximately 3 MHz.

14. The treatment system of claim 1, wherein said ultrasound apparatus is operational at a frequency of approximately 1 MHz.

15. The treatment system of claim 1, wherein pressure exertion is provided on said region of treatment during said transmission of ultrasound waves.

16. The treatment system of claim 15, wherein said pressure exertion comprises manual pressure with a transducer head of said ultrasound apparatus against said region of treatment.

17. The treatment system of claim 16, wherein said transducer head is used to provide a massaging action to said region of treatment.

18. The treatment system of claim 17, wherein said massaging action comprises moving said transducer head in ways selected from the list consisting of: small circular motions all the while keeping the wrist straight, and tilting and moving the wrist in different directions repetitively.

19. The treatment system of claim 15, wherein said pressure exertion comprises mechanical massaging.

20. The treatment system of claim 15, wherein said pressure exertion comprises manual massaging.

21. The treatment system of claim 15, wherein said pressure exertion comprises a massage given by bare hands.

22. The treatment system of claim 1, wherein said electrical stimulation apparatus is operational in an intensity range between 5 mA to 90 mA.

23. The treatment system of claim 1, wherein said electrical stimulation apparatus is operational in a frequency range between 5 Hz to 150 Hz.

24. The treatment system of claim 1, wherein said interferential stimulation is selected from the list consisting of:
   premodulated;
   biphasic;
   interferential (I/F) isoplanar (4 poles);
   interferential (I/F) vectorial (4 poles); and
   medium frequency (M/F).

25. The treatment system of claim 1, wherein said interferential stimulation is used in a pattern variation, wherein said pattern variation lasts for varying durations, wherein said pattern variation comprises changing said interferential stimulation during a treatment session.

26. The treatment system of claim 23, wherein the frequency of operation of said electrical stimulation apparatus is varied over time within said frequency range.

27. The treatment system of claim 26, wherein said variation over time of said operational frequency of said electrical stimulation apparatus is selected from the list consisting of:
   applying a first frequency for a fixed amount of time before switching to a second frequency;
   gradually changing frequencies from a first frequency to a second frequency over various time durations; and
   intermittently applying extreme frequencies within said frequency range.

28. The treatment system of claim 1, wherein said ultrasound apparatus is used in conjunction with a gel rubbed on said region of treatment.

29. The treatment system of claim 1, further comprising a camera.

30. The treatment system of claim 1, further comprising a processor.

31. The treatment system of claim 1, further comprising a measuring apparatus.

32. The treatment system of claim 31, wherein said measuring apparatus further comprises a pressure gauge.

33. A treatment method for reducing body perimeter comprising the procedures of:
   transmitting ultrasound waves to a region of treatment, at an intensity of between 1.5 to 3 W/cm$^2$, wherein the operational frequency of said ultrasound waves is varied over time during a treatment session; and
   applying electrical stimulation to said region of treatment, wherein said electrical stimulation comprises interferential stimulation, and the operational frequency of said interferential stimulation is varied over time during said treatment session;
   varying said operational frequency of said ultrasound waves at a rate that is inversely proportional to a rate at which said operational frequency of said interferential stimulation is varied during the same treatment session.

34. The treatment method of claim 33, wherein said reduction of body perimeter comprises reducing or eliminating cellulite.

35. The treatment method of claim 33, wherein said reduction of body perimeter comprises reducing body fat.

36. The treatment method of claim 33, wherein said reduction of body perimeter is utilized for the body of a human or an animal.

37. The treatment method of claim 33, wherein said area of treatment comprises regions of the body selected from the list consisting of: legs, thighs, knees, buttocks, abdomen, and arms.

38. The treatment method of claim 33, wherein said treatment method is utilized for reducing and eliminating post-pregnancy stretch marks on the abdomen and mid-sections of women.

39. The treatment method of claim 33, wherein said treatment method is utilized for reducing and eliminating at least one selected from the list consisting of: sagging skin; skin having stretch marks on it, and skin affected by cellulite.

40. The treatment method of claim 39, wherein said sagging skin comprises sagging upper arm skin.

41. The treatment method of claim 33, wherein said treatment method is utilized for at least one of the list consisting of:
   rendering the general appearance of said sagging skin to look and feel smooth;
   returning said appearance of said sagging skin to the state it appeared before sagging.

42. The treatment method of claim 33, wherein said procedure of transmitting ultrasound waves comprises transmitting ultrasound waves at a frequency ranging between 1 to 4 MHz.

43. The treatment method of claim 33, wherein said ultrasound waves are transmitted for a duration of 40 to 45 minutes.

44. The treatment method of claim 33, wherein said ultrasound waves are transmitted at a frequency of approximately 3 MHz.

45. The treatment method of claims 33, wherein said ultrasound waves are transmitted at a frequency of approximately 1 MHz.

46. The treatment method of claim 33, wherein pressure exertion is provided on said region of treatment during said transmission of ultrasound waves.

47. The treatment method of claim 46, wherein said pressure exertion comprises manual pressure with a transducer head of an ultrasound apparatus against said region of treatment.

48. The treatment method of claim 47, wherein said transducer head is used to provide a massaging action to said region of treatment.

49. The treatment method of claim 48, wherein said massaging action comprises moving said transducer head in ways selected from the list consisting of:

small circular motions all the while keeping the wrist straight; and tilting and moving the wrist in different directions repetitively.

50. The treatment method of claim 46, wherein said pressure exertion comprises mechanical massaging.

51. The treatment method of claim 46, wherein said pressure exertion comprises manual massaging.

52. The treatment method of claim 46, wherein said pressure exertion comprises a massage given by bare hands.

53. The treatment method of claim 33, wherein said procedure of applying electrical stimulation comprises applying electrical stimulation at an intensity range between 5 mA to 90 mA.

54. The treatment method of claim 33, wherein said procedure of applying electrical stimulation comprises applying electrical stimulation at a frequency range between 5 Hz to 150 Hz.

55. The treatment method of claim 33, wherein said interferential stimulation is selected from the list consisting of:
premodulated;
biphasic;
interferential (I/F) isoplanar (4 poles);
interferential (I/F) vectorial (4 poles); and
medium frequency (M/F).

56. The treatment method of claim 33, wherein said interferential stimulation is used in a pattern variation, wherein said pattern variation lasts for varying durations, and wherein said pattern variation comprises changing said interferential stimulation during a treatment session.

57. The treatment method of claim 33, wherein said variation over time of said operational frequency of the interferential stimulation is selected from the list consisting of:
applying a first frequency for a fixed amount of time before switching to a second frequency;
gradually changing frequencies from a first frequency to a second frequency over various time durations; and
intermittently applying extreme frequencies within said frequency range.

58. The treatment method of claim 33, further comprising the procedure of applying a gel rubbed on said region of treatment in conjunction with said transmission of ultrasound waves.

59. The treatment method of claim 33, further comprising the procedure of recording said treatment using a camera.

60. The treatment method of claim 59, further comprising the procedure of using a processor for controlling said electrical stimulation, said ultrasound waves, and said camera, and for recording a patient's measurements.

61. The treatment method of claim 33, further comprising the procedure of measuring said body perimeter for determining reduction thereof, said procedure of measuring comprising the sub-procedures of:
standing a patient in an upright position, with said patient's arms down in order to maintain a consistent posture;
measuring and recording the height of a region of treatment from the floor in order to maintain a consistent vertical point from the floor at which a circumference measurement is taken;
measuring said region of treatment using a measuring apparatus with a pressure gauge attached to it in order to maintain a constant pressure on the skin;
measuring said region of treatment in a horizontal fashion, such that said measuring apparatus is placed around said region of treatment in a plane parallel to the floor on which said patient is standing;
measuring said region of treatment using said measuring apparatus with said pressure gauge attached to it with a given pressure exerted on said region of treatment and recording said measurement; and
measuring said region of treatment a subsequent time thereafter using said measuring apparatus with said pressure gauge attached to it at said height of said region of treatment from the floor with said given pressure exerted on said region of treatment, with said measuring apparatus being in a horizontal plane to the floor while measuring said region of treatment.

* * * * *